United States Patent [19]

Fowlkes et al.

[11] Patent Number: 6,059,727
[45] Date of Patent: May 9, 2000

[54] METHOD AND APPARATUS FOR COMPOSITION AND DISPLAY OF THREE-DIMENSIONAL IMAGE FROM TWO-DIMENSIONAL ULTRASOUND SCAN DATA

[75] Inventors: J. Brian Fowlkes; Paul L. Carson; Aaron Moskalik, all of Ann Arbor, Mich.; Jian-Feng Chen, Issaquah, Wash.; Jonathan M. Rubin, Ann Arbor, Mich.

[73] Assignee: The Regents of the University of Michigan, Ann Arbor, Mich.

[21] Appl. No.: 08/981,058

[22] PCT Filed: Jun. 14, 1996

[86] PCT No.: PCT/US96/10189

§ 371 Date: Apr. 13, 1998

§ 102(e) Date: Apr. 13, 1998

[87] PCT Pub. No.: WO97/00482

PCT Pub. Date: Jan. 3, 1997

Related U.S. Application Data

[60] Provisional application No. 60/000,257, Jun. 15, 1995.

[51] Int. Cl.⁷ ..................................................... A61B 8/00
[52] U.S. Cl. ........................................... 600/443; 128/916
[58] Field of Search ............................ 128/916; 600/443, 600/455, 456, 442; 356/28.5

[56] References Cited

U.S. PATENT DOCUMENTS

| | | | |
|---|---|---|---|
| 4,322,162 | 3/1982 | McKelvie et al. | 356/35.5 |
| 4,435,984 | 3/1984 | Gruber | 73/628 |
| 4,770,184 | 9/1988 | Greene, Jr. et al. | 128/661.08 |
| 4,967,093 | 10/1990 | Takemori | 250/560 |
| 5,000,183 | 3/1991 | Bonnefous | 128/660.01 |
| 5,049,987 | 9/1991 | Hoppenstein | 358/88 |
| 5,061,860 | 10/1991 | Takemori | 250/561 |
| 5,127,409 | 7/1992 | Daigle | 128/660.07 |
| 5,287,435 | 2/1994 | Cohen et al. | 395/118 |
| 5,305,756 | 4/1994 | Entrekin et al. | 128/660.09 |
| 5,365,929 | 11/1994 | Peterson | 128/661.1 |
| 5,370,120 | 12/1994 | Oppelt et al. | 128/660.03 |
| 5,390,674 | 2/1995 | Robinson et al. | 128/660.07 |
| 5,390,677 | 2/1995 | Ferrera et al. | 128/661.09 |
| 5,396,890 | 3/1995 | Weng | 128/660.07 |
| 5,412,763 | 5/1995 | Knoplioch et al. | 395/124 |
| 5,426,498 | 6/1995 | Brueck et al. | 356/35.5 |
| 5,471,990 | 12/1995 | Thirsk | 128/661.09 |
| 5,474,073 | 12/1995 | Schwartz et al. | 128/661.1 |
| 5,476,097 | 12/1995 | Robinson | 128/660.05 |
| 5,485,842 | 1/1996 | Quistgaard | 128/66.07 |
| 5,582,173 | 12/1996 | Li | 128/660.07 |
| 5,655,535 | 8/1997 | Friemel et al. | 600/443 |
| 5,876,342 | 3/1999 | Chen et al. | 600/443 |
| 5,876,343 | 3/1999 | Teo | 600/443 |

OTHER PUBLICATIONS

Adler et al., "Doppler Ultrasound Color Flow Imaging in the Study of Breast Cancer: Preliminary Findings," Ultrasound in Medicine and Biology, 1990, vol. 16, No. 6, pp. 553–559.

Adler et al., "Ultrasonic Estimation of Tissue Perfusion: A Stochastic Approach," Ultrasound in Medicine and Biology, 1995; vol. 21, No. 4, pp. 493–500.

Anderson et al., "CT Techniques," Computed Body Tomography with MRI Correlation, 2nd Edition, Lee et al, editors, New York, NY: Raven, 1989; pp. xiii, 31, 46–50.

(List continued on next page.)

*Primary Examiner*—Marvin M. Lateef
*Assistant Examiner*—Ali M. Imam
*Attorney, Agent, or Firm*—Arnold White & Durkee

[57] ABSTRACT

A 3D image data set representing a volume of material such as human tissue is created using speckle decorrelation techniques to process successive 2D data slices from a moving, standard 1D or 1.5D ultrasound transducer. This permits the use of standard ultrasound machinery, without the use of additional slice-position hardware, to create 3D images without having to modify the machinery or its operation. Similar techniques can be used for special data processing within the imaging system as well to expedite the image acquisition process. Optionally, the image quality of 2D images can be enhanced through the use of multiple 3D data sets derived using the method.

35 Claims, 6 Drawing Sheets

OTHER PUBLICATIONS

Atkinson et al., "Random Noise in Ultrasonic Echoes Diffracted by Blood," Journal of Physics A: Mathematical Nuclear and General, 1974, vol. 7, No. 11, pp. 1293–1302.

Axel, "Cerebral Blood Flow Determination by Rapid–Sequence Computed Tomography: A Theoretical Analysis," Radiology, 1980, vol. 137, No. 3, pp. 679–686.

Bamber et al., "Parametric Imaging of Tissue Shear and Flow Using B–Scan Decorrelation Rate," (Abstract), Journal of Ultrasound Medicine, 1988; vol. 7, No. 10, pp. S135–S136.

Berman et al., "Sonographic Evaluation of Acute Intrascrotal Pathology," American Journal of Roentgenology, Apr. 1996, vol. 166, pp. 857–861.

Bourne et al., "Transvaginal Colour Flow Imaging: A Possible New Screening Technique for Ovarian Cancer," British Medical Journal, 1989, vol. 299, pp. 1367–1370.

Bragg et al., "Radiologic Techniques in Cancer," Cancer: Principles & Practice of Oncology, 3rd Edition, Devita, Jr. et al., editors, Philadelphia, PA: Lippincott, 1989, pp. 440–463.

Brenner et al., "Elements of Normal Renal Function: The Renal Circulations," The Kidney, 3rd Edition, Brenner et al., editors, Philadelphia, PA: Saunders, 1986, pp. 114–118.

Burns et al., "Power Doppler Imaging Combined with Contrast–Enhancing Harmonic Doppler: New Method for Small–Vessel Imaging," (Abstract), Radiology, 1994, vol. 193(P), p. 366.

Burns, "Hemodynamics," Clinical Applications of Doppler Ultrasound, Taylor et al., editors, New York, NY: Raven, 1988, pp. 46–75.

Carson et al., "Approximate Quantification of Detected Fractional Blood Volume and Perfusion from 3–D Color Flow and Doppler Power Signal Imaging," Levy et al., editors, Proceedings of the 1993 IEEE Ultrasonics Symposium, Baltimore, Maryland, Oct. 31–Nov. 3, 1993; Catalog No. 93CH3301–9, vol. 2, pp. 1023–1026.

Castagnone et al., "Color Doppler Sonography in Graves' Disease: Value in Assessing Activity of Disease and Predicting Outcome," American Journal of Roentgenology, Jan. 1996, vol. 166, pp. 203–207.

Coley et al., "Acute Testicular Torsion: Comparison of Unenhanced and Contrast–Enhanced Power Doppler US, Color Doppler US, and Radionuclide Imaging," Radiology, 1996, vol. 199, No. 2, pp. 441–446.

Cosgrove et al., Breast Diseases: Color Doppler US in Differential Diagnosis, Radiology, 1993, vol. 189, pp. 99–104.

Cosgrove et al., "Color Doppler Signals from Breast Tumors," (work in progress), Radiology, 1990, vol. 176, pp. 175–180.

Dixon et al., "Colour Doppler Ultrasonography Studies of Benign and Malignant Breast Lesions," The British Journal of Surgery, 1992, vol. 79, pp. 259–260.

Downey et al., "Three–Dimensional Power Doppler Detection of Prostatic Cancer," American Journal of Roentgenology, 1995, vol. 165, p. 741.

Downey et al., "Vascular Imaging with a Three–Dimensional Power Doppler System," American Journal of Roentgenology, 1995, vol. 165, pp. 665–668.

Dymling et al., "Measurement of Blood Perfusion in Tissue Using Doppler Ultrasound," Ultrasound in Medicine and Biology, 1991, vol. 17, No. 5, pp. 433–444.

Faran, "Sound Scattering by Solid Cylinders and Spheres," The Journal of the Acoustical Society of America, 1951, vol. 23, No. 4, pp. 405–418.

Folkman, "Tumor Angiogenesis," Advances in Cancer Research, vol. 43, Klein et al, editors, Academic Press, Inc., 1985, pp. 175–203.

Hottinger et al., "Blood Flow Measurement Using the Attenuation–Compensated Volume Flowmeter," Ultrasonic Imaging, 1979, vol. 1, No. 1, pp. 1–15.

Huber et al., "Breast Tumors: Computer–Assisted Quantitative Assessment with Color Doppler US," Radiology, 1994, vol. 192, No. 3, pp. 797–801.

Kabas et al., "Intraoperative Perfusion Contrast Echocardiography; Initial Experience During Coronary Artery Bypass Grafting," The Journal of Thoracic and Cardiovascular Surgery, 1990, vol. 99, No. 3, pp. 536–542.

Kedar et al., "Automated Quantification of Color Doppler Signals: A Preliminary Study in Breast Tumors," Radiology, 1995, vol. 197, No. 1, pp. 39–43.

Kedar et al., "Microbubble Contrast Agent for Color Doppler US: Effect on Breast Masses," (work in progress), Radiology, Mar. 1996, vol. 198, No. 3, pp. 679–686.

Kelly et al., "Prostate Cancer and the Role of Color Doppler US," Radiology, 1993, vol. 189, No. 1, pp. 153–156.

Kremer et al., "Ultrasonic in Vivo and in Vitro Studies on the Nature of the Ureteral Jet Phenomenon," Radiology, 1982, vol. 142, No. 1, pp. 175–177.

Ladefoged et al., "Renal Blood Flow, Circulation Times and Vascular Volume in Normal Man Measured by the Intraarterial Injection—External Counting Technique," Acta Physiologica Scandinavica, 1967, vol. 69, pp. 220–229.

Luker et al., "Pediatric Testicular Tumors: Evaluation with Gray–Scale and Color Doppler US," Radiology, 1994, vol. 191, No. 2, pp. 561–564.

Luker et al., "Scrotal US in Pediatric Patients: Comparison of Power and Standard Color Doppler US," Radiology, Feb. 1996, vol. 198, No. 2, pp. 381–385.

Newman et al., "Detection of Soft–Tissue Hyperemia: Value of Power Doppler Sonography," American Journal of Roentgenology, 1994, vol. 163, pp. 385–389.

Newman et al., "Prostate Cancer: Diagnosis with Color Doppler Sonography with Histologic Correlation of Each Biopsy Site," Radiology, 1995, vol. 195, No. 1, pp. 86–90.

Newman et al., "Power Doppler Sonography of Synovitis: Assessment of Therapeutic Response—Preliminary Observations," Radiology, Feb. 1996, vol. 198, No. 2, pp. 582–584.

Paulson et al., "Diagnosis of Acute Cholecystitis with Color Doppler Sonography: Significance of Arterial Flow in Thickened Gallbladder Wall," American Journal of Roentgenology, 1994, vol. 162, pp. 1105–1108.

Price et al., "Ultrasound Detection of Differences in Density Explanation of the Ureteric Jet Phenomenon and Implications for New Ultrasound Applications," Investigative Radiology, 1989, vol. 24, No. 11, pp. 876–883.

Rempp et al., "Quantification of Regional Cerebral Blood Flow and Volume with Dynamic Susceptibility Contrast–Enhanced MR Imaging," Radiology, 1994, vol. 193, No. 3, pp. 637–641.

Rifkin et al., "Prostate: Techniques, Results, and Potential Applications of Color Doppler US Scanning," Radiology, 1993, vol. 186, No. 2, pp. 509–513.

Rubin et al., "Fractional Moving Blood Volume: Estimation with Power Doppler US," Radiology, 1995, vol. 197, No. 1, pp. 183–190.

Rubin et al., "Power Doppler US: A Potentially Useful Alternative to Mean Frequency–Based Color Doppler US," Radiology, 1994; vol. 190, No. 3, pp. 853–856.

Rubin et al., "Visualization of Tumor Vascularity in a Rabbit VX2 Carcinoma by Doppler Flow Mapping," Journal of Ultrasound Medicine, 1987, vol. 6, No. 3, pp. 113–120.

Schrope et al., "Second Harmonic Ultrasonic Blood Perfusion Measurement," Ultrasound in Medicine and Biology, 1993; vol. 19, No. 7, pp. 567–579.

Selkurt, "The Renal Circulation," Handbook of Physiology, Section 2: Circulation, vol. II, Hamilton et al., editors, Washington, DC: American Physiological Society, 1963, pp. 1457–1516.

Shimamoto et al., "Intratumoral Blood Flow: Evaluation with Color Doppler Echography," Radiology, 1987, vol. 165, No. 3, pp. 683–685.

Shmulewitz et al., "Temperature–Dependent Ultrasound Color Flow Doppler Imaging in the Study of a VX2 Tumor in Rabbits: Preliminary Findings," Ultrasound in Medicine and Biology, 1993, vol. 19, No. 3, pp. 221–229.

Shung et al., "The Effects of Hematocrit, Shear Rate, and Turbulence on Ultrasonic Doppler Spectrum from Blood," IEEE Transactions on Biomedical Engineering, 1992, vol. 39, No. 5, pp. 462–469.

Shung et al., "Ultrasound Scattering Properties of Blood," Intravascular Ultrasound, Developments in Cardiovascular Medicine, Roelandt et al., editors, The Netherlands: Kluwer Academic Publishers, 1993, pp. 119–139.

Shung, "In Vitro Experimental Results on Ultrasonic Scattering in Biological Tissues," Ultrasonic Scattering in Biological Tissues, Shung et al., editor, Boca Raton, FL: CRC Press, 1993, pp. 291–312.

Sohn et al., "Die dopplersonographische Untersuchung von Mammatumoren mit Hilfe der Farbdopplersonographie, der Duplexsonographie und des CW–Dopplers" (English translation attached: "Doppler Ultrasonographic Examinations of Breast Tumors Using Color Doppler, Duplex, and Continuous–Wave Doppler Ultrasonography", pp. 1–17), Zentralblatt für Gynäkologie, 1992, 114:249–253.

Tanaka et al., "Color Doppler Flow Imaging of Liver Tumors," American Journal of Roentgenology, 1990, vol. 154, pp. 509–514.

Teefey et al., "Bowel Wall Thickening: Differentiation of Inflammation from Ischemia with Color Doppler and Duplex US," Radiology, Feb. 1996, vol. 198, No. 2, pp. 547–551.

Watson et al., "Contrast Agents," Magnetic Resonance Imaging, Stark et al., editors, St Louis, MO: Mosby Year Book, 1992, pp. 413–421.

Weidner et al., "Tumor Angiogenesis and Metastasis—Correlation in Invasive Breast Carcinoma," The New England Journal of Medicine, 1991, vol. 324, No. 1, pp. 1–8.

Wilson et al., "A Feasibility Study on Quantitating Myocardial Perfusion with Albunex, and Ultrasonic Contrast Agent," Ultrasound in Medicine and Biology, 1993; vol. 19, No. 3, pp. 181–191.

Carson et al., "Scan–Plan and Compound 3D Registration System for Battlefield Trauma Imaging," Concept Paper SOL BAA 95–27 (1995), pp. 1–5.

Carson et al., HHS/PHS Grant Application 95–1155, "Enhanced Color Flow Imaging of Breast Cancer," 1994 (face page and pp. 2–3, 48, 63, 68–72).

Carson et al., "Image–Based Slice Positioning Disclosure," Dec. 12, 1994, pp. 3–11 and Figs.

Chen et al., "A Comparison of the Motion Tracking of 2–D Ultrasonic B–Mode Tissue Images with a Calibrated Phantom," Proceedings of the 1991 IEEE Ultrasonics Symposium, Lake Buena Vista, Florida, Dec. 8–11, 1991; Catalog No. 91CH3079–1, vol. 2, pp. 1211–1214.

Chen et al., "Ultrasound Tissue Displacement Imaging with Application to Breast Cancer," Ultrasound in Medicine and Biology, 1995, vol. 21, No. 9, pp. 1153–1162.

Chen et al., "The Accuracy and Precision of Estimating Tissue Displacements from Ultrasonic Images," McAvoy, Editor, Proceedings of the 1992, IEEE Ultrasonics Symposium, Tucson, Arizona, Oct. 20–23, 1992; Catalog No. 92CH3118–7, vol. 2, pp. 1069–1072.

Chen et al., "Determination of Scanhead Motion Using Decorrelation of Speckle," (Abstract) Medical Physics, 1995, vol. 22, No. 6, p. 974.

Chen et al., "Determination of Scan–Plane Motion Using Speckle Decorrelation: Theoretical Considerations and Initial Test," Internat. J. Imaging Systems and Technology, vol. 8, pp. 38–44 (1997).

Detmer et al., "3D Ultrasonic Image Feature Localization Based on Magnetic Scanhead Tracking: In Vitro Calibration and Validation," Ultrasound in Medicine and Biology, 1994, vol. 20, No. 9, pp. 923–936.

Fowlkes et al., "An Examination of Ultrasound Measured Tissue Perfusion in Breast Cancer," U.S. Army Status Report, Jul. 1, 1995; Grant No. DAMD17–94–J4144. Cover sheets and pp. 1–14.

Moskalik et al., "Image–Based Regulation (IBaR) for Positioning Ultrasound Images in Three Dimension," (Abstract) Journal of Ultrasound Medicine, 1996, vol. 15, p. S34.

Nelson et al., "Determination of Transducer Position from Backscattered Signal Intensity," (Abstract) Journal of Ultrasound Medicine, 1996, vol. 15, p. S77.

Tuthill et al., "Automated 3–D US Frame Positioning Computed from Elevational Speckle Decorrelation," manuscript accepted for publication in Radiology (1998).

TWO ORTHOGONAL 3D SCANS - IRREGULAR IMAGE SPACING

TOP VIEW OF PLANE INTERSECTIONS

EACH GRID POINT IS THE MAXIMUM CORRELATION VALUE FOR THE CORRESPONDING AMODE LINES IN THE TWO ORTHOGONAL PLANES.

SEARCH REGION TO DEFINE THE INTERSECTION OF HIGHLIGHTED IMAGE PLANES.

DIAGRAM OF A MODE CORRELATION FOR SLICE POSITIONING

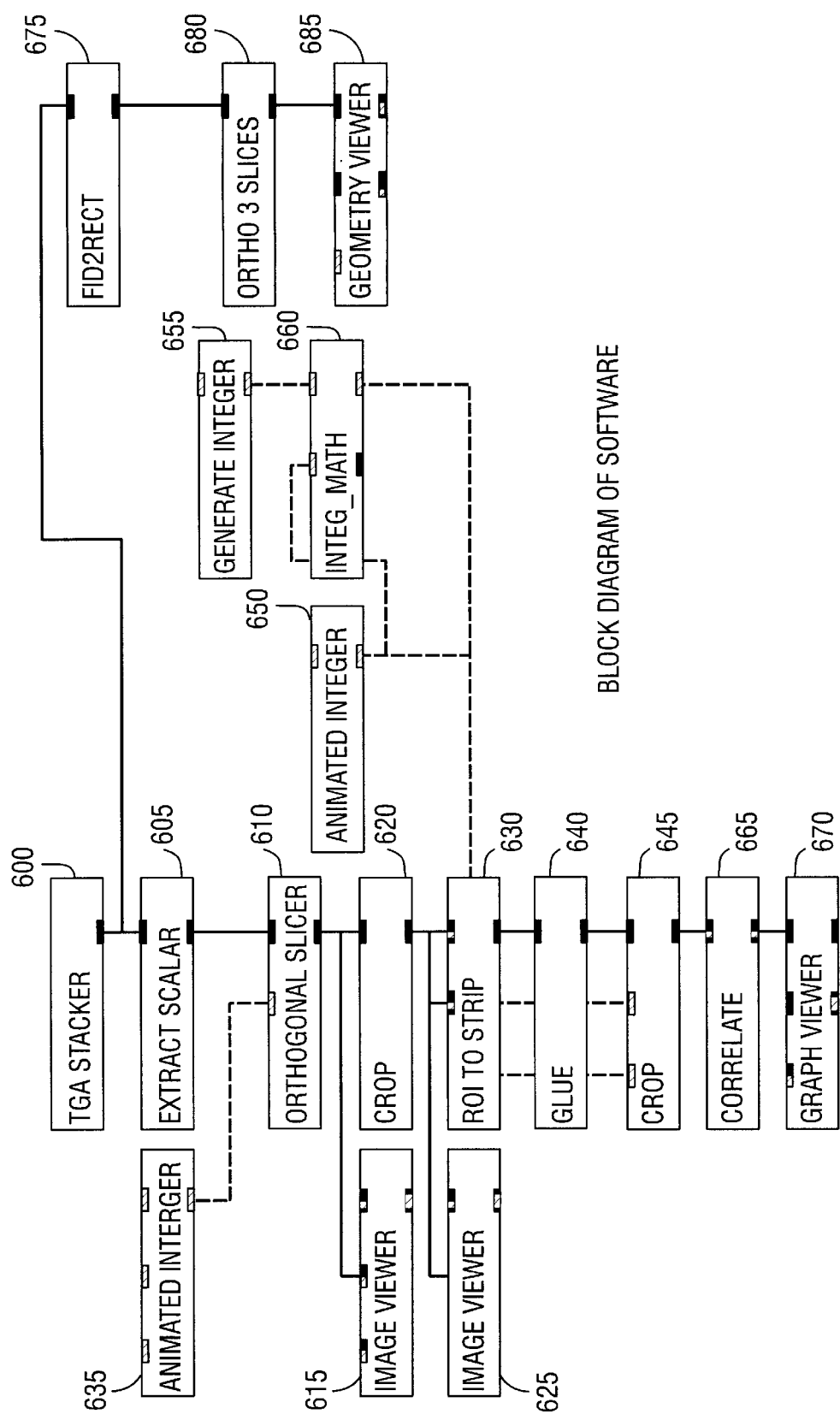

METHOD AND APPARATUS FOR COMPOSITION AND DISPLAY OF THREE-DIMENSIONAL IMAGE FROM TWO-DIMENSIONAL ULTRASOUND SCAN DATA

CROSS REFERENCE TO RELATED APPLICATION

This application claims the benefit of U.S. Provisional Application No. 60/000,257 filed Jun. 15, 1995.

This invention was made in part with government support under Grant No. CA55076 awarded from the National Institute of Health and Grant No. DAMD 12-94-K-4144 awarded by the Department of the Army. The United States government has certain rights in this invention.

BACKGROUND OF THE INVENTION

The invention described below was made in part with government support. The United States government has certain rights in the invention.

As well-known to those of ordinary skill, a standard real-time two-dimensional (2D) ultrasound scan typically entails the following. Referring to FIG. 1, an operator holds a transducer 100 in one position relative to a volume of material 102, e.g., human tissue. The transducer 100 is sometimes referred to as a scanhead; it commonly has an essentially linear, one-dimensional (1D) shape, although scanheads of round or other shapes are also known, and emits a beam of ultrasound energy toward the material 102 within a "scan plane" 103. The ultrasound energy is reflected from the material 102 and detected by the scanhead, which generates data signals representative of the detected energy. A conventional ultrasound machine 105 receives and processes the resulting data from the scanhead 100 and displays a 2D image of the tissue volume 102 being scanned, e.g., on a video display terminal 107, a film camera, or other hard copy device (not shown). Movement of the scanhead 100 results in different 2D views of the tissue volume 102 being presented.

Three-Dimensional (3D) data can be derived from a series of 2D views taken from different angles or positions. These views are sometimes referred to as "slices" of the actual three-dimensional tissue volume 102; the data sets used to generate these views are referred to here as "data slices." Experienced radiologists and similarly trained personnel can often mentally correlate a series of 2D images derived from these data slices to obtain useful 3D information. For example, a radiologist observing a scan of 2D views of a pregnant woman's abdomen may be able to diagnose the fetus's cleft palate by repeatedly moving the scanhead 100 and mentally correlating the 2D images presented.

Automated 3D image reconstruction has been done in the past by (a) using mechanical or other means of encoding the successive positions of the scanhead 100 as it is moved about the tissue volume 102, and (b) processing this additional encoded data to provide an indication of the relative positions of the 2D images acquired. This is often difficult to do on a real-time basis. Several technical problems have restricted the use of such systems, including noise interference and limits on spatial resolution. A related approach is to force the scanhead 100 to move over a predetermined track, but that can be adversely affected by movement of the material 102, which often happens in scanning human bodies.

Efforts are already being made by some ultrasound scanner manufacturers and others to produce specialized 2D hardware for 3D imaging. Such 2D hardware can be expensive to produce and cumbersome to use, with problems including the current cost and size of the scanhead, image artifacts produced by the fluid path used, etc. Replacing the current 1D arrays with full 2D arrays for making true 3D images is not yet practical due to the number of elements that would be required in the transducer, connections to these and the electronic channels required to services the additional elements. The ultrasound industry is presently interested in the potential for 3D imaging technology which would not obviate the current cost advantage of 1D scanheads.

Speckle Tracking of Moving Tissues

The invention described and claimed below makes a novel use of image analysis, or analysis of RF (radio frequency) data used to create ultrasound images, to indicate the relative position of such images in a three dimensional data set. For example, in one implementation, a speckle correlation technique is used that is well-known in other contexts: When a source of coherent energy (e.g., a laser or an ultrasound beam) interacts with a collection of scatterers, the amplitude of the reflected signal varies in relation to the relative positions of the scatterers. Displayed visually, this amplitude variation appears as a speckle pattern.

Ultrasound speckle correlation techniques have been used to determine the movement of blood. Consider an example: Suppose that the material 102 is a human blood vessel with blood cells moving through it. The blood cells are scatterers of the ultrasound energy generated by the scanhead 100, meaning that the amplitudes of the reflected signals vary in relation to the relative positions of the blood cells.

The blood cells are continuously circulating in the body, however. Consequently, specific blood cells are continuously moving out from under the scanhead 100 (and out of the ultrasound energy beam) and being replaced by others.

As a result, the speckle pattern of the reflected signal is continuously changing because of the movement of the blood cells. This is referred to as "decorrelation" of the signal with respect to the original speckle pattern. By monitoring the amount of decorrelation using standard techniques, the rate at which blood moves under the scanhead may be monitored.

The invention described and claimed below was developed in the course of efforts to create 3D images of the breast, to improve the quality of breast cancer diagnosis. It proved difficult to obtain 3D ultrasound images of breasts using conventional mechanical registration of scanhead position. The difficulty was particularly acute for small, dense breasts, which are well recognized as also presenting problems for X-ray mammography diagnosis.

SUMMARY OF THE INVENTION

In a novel adaptation of decorrelation techniques used for monitoring blood perfusion, a 3D image data set representing a volume of material such as human tissue is created using successive 2D data slices from a moving, standard 1D or 1.5D ultrasound transducer. (The term "1.5D" refers to the use of a limited number of separate elements in a second dimension.) This permits the use of standard ultrasound machinery, without the use of additional slice-position hardware, to create 3D images without having to modify the machinery or its operation. Similar techniques can be used for special data processing within the imaging system as well to expedite the image acquisition process.

Optionally, the image quality of 2D images can be enhanced through the use of multiple 3D data sets derived using the method.

BRIEF DESCRIPTION OF THE DRAWINGS

FIG. 6 is a block diagram of software modules used in one implementation of the invention.

DETAILED DESCRIPTION OF THE PREFERRED EMBODIMENTS

A Post-Processing Implementation

Figure 1:
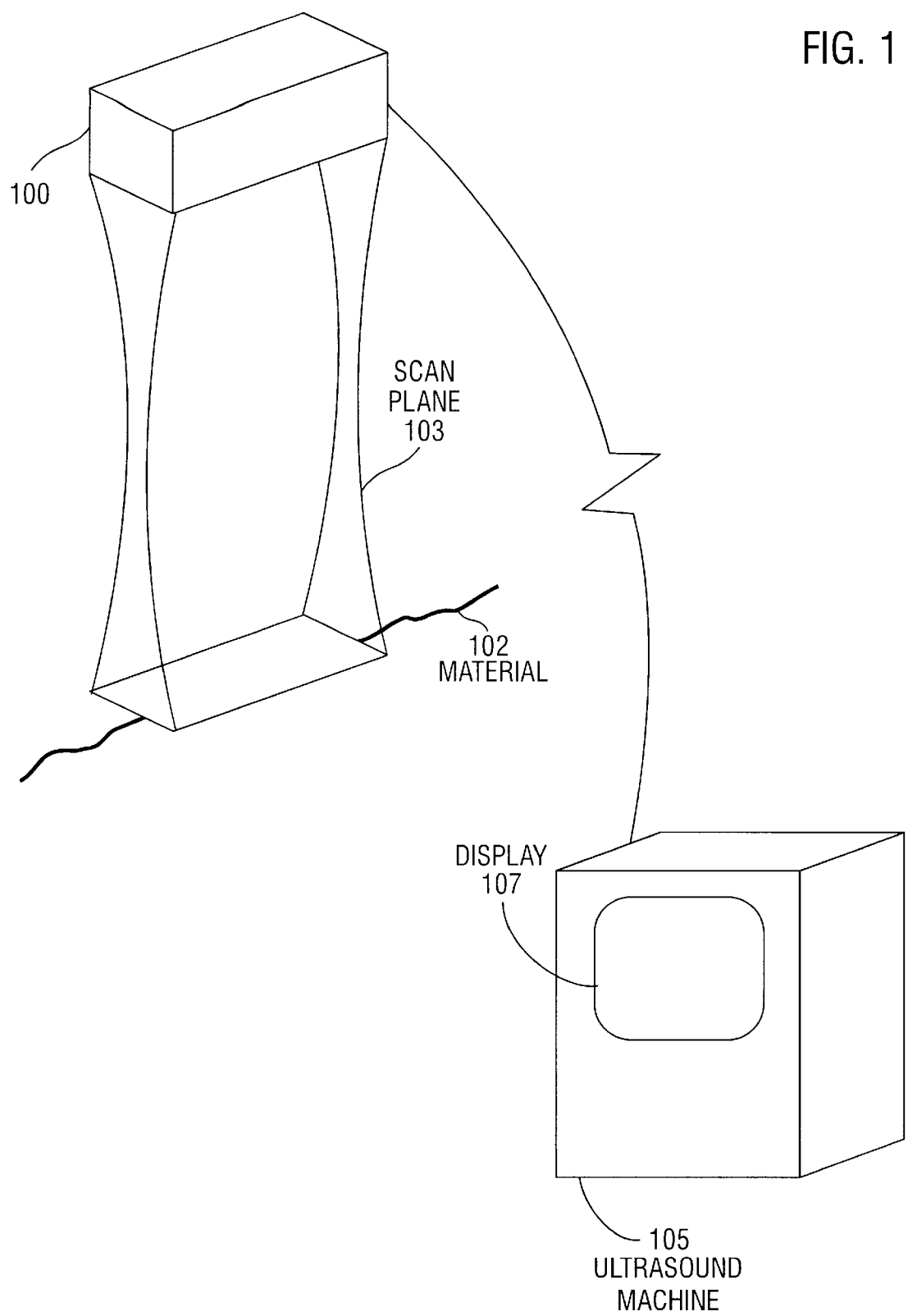
FIG. 1 is a simplified perspective view of an ultrasound scanner being used to scan a material.
Figure 2:
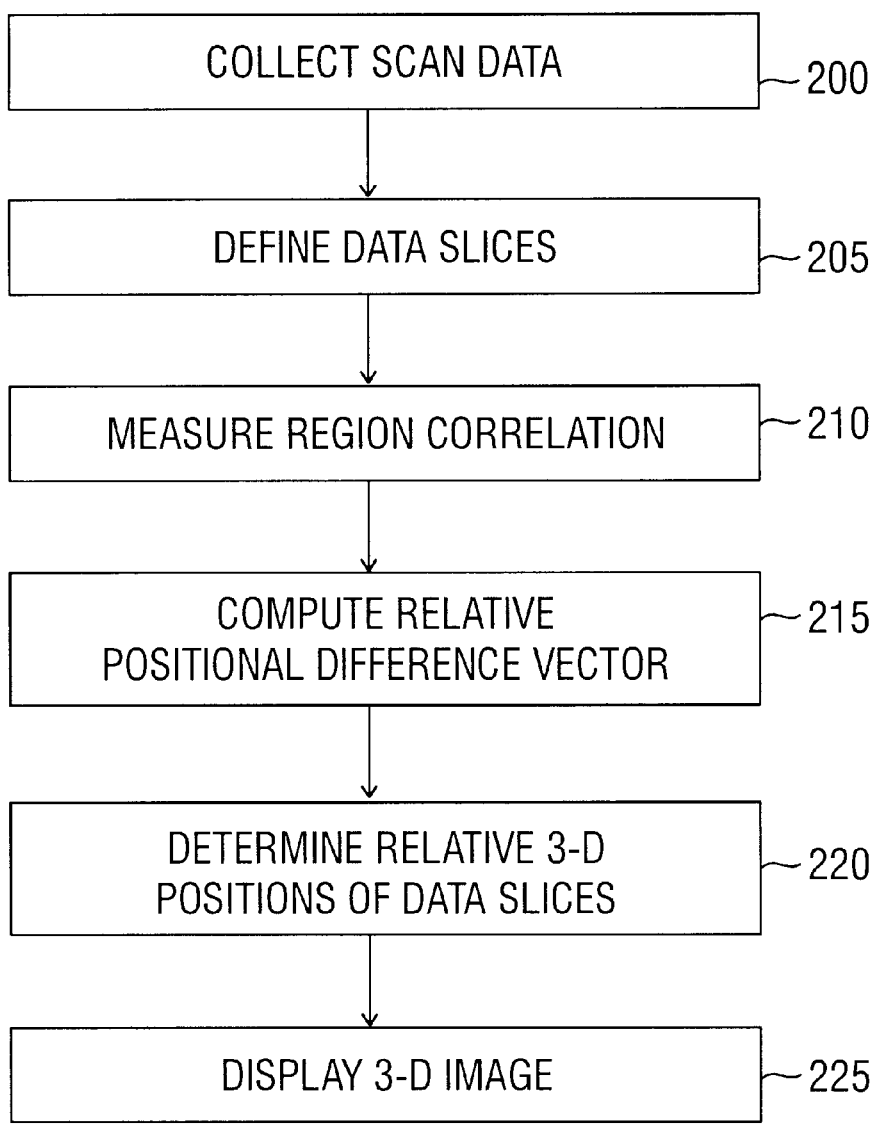
FIG. 2 is a flow chart depicting the operations performed in a method in accordance with the invention.

An illustrative implementation of a method in accordance with the invention is depicted in flow-chart form in FIG. 2. At block 200, data acquired by ultrasound scanning of a material 102 using a scanhead 100 are collected into a computer memory for post-processing by a computer or other machine, e.g., by a programmable ultrasound machine 105 loaded with a suitable computer program or programs. The material in question may be a volume of human tissue or any other material suitable for ultrasound scanning, as well known in the art.

The scanning process itself generates a series of signals encoding data representing physical two-dimensional "slices" of the material being scanned. At block 205, data encoded in signals corresponding to the respective slices of the material are defined and referred to for convenience as data slices. One or more regions is defined within a first data slice, referred to as data slice 1. Similarly, one or more regions is defined within another data slice, referred to as data slice 2.

At block 210, the amounts of correlation between the respective regions in data slice 1 and data slice 2 are conventionally determined. For example, suppose that data slice 1 is divided into regions 1a, 1b, etc., and data slice 2 is divided into regions 2a, 2b, etc. The amount of correlation between regions 1a and 2a is determined, as is the amount of correlation between regions 1b and 2b, etc. The respective amounts of decorrelation may be determined by a process of speckle decorrelation measurement as known to those of ordinary skill.

At block 215, the respective amounts of correlation between the regions are used to compute, in conventional fashion, a relative positional difference vector that represents a relative positional difference between data slice 1 and data slice 2. Those of ordinary skill having the benefit of this disclosure will recognize that the relative positional difference vector could be a scalar, i.e., a one-dimensional vector.

Data representations of at least a portion of data slice 1, at least a portion of data slice 2, and the computed relative positional difference vector may be stored in a memory device, e.g., RAM or a disk storage device in a computer, for future use. Those of ordinary skill having the benefit of this disclosure will recognize that the data representations may be preprocessed if desired before storage, e.g., by conventionally "compressing" the data for greater storage efficiency. Such compression might include, e.g., storing, as the representation of a given data slice, a vector representing a change from a different data slice. Other compression techniques such as the well-known LZW method may also be used.

At block 220, from the relative positional difference vector, a computation is made to determine the relative positions of data slice 1 and data slice 2 within a 3D image of the material. The 3D image is conventionally displayed on a visual display such as a video display terminal, a computer printout, a computer-generated photograph, etc.

Optionally, portions of the data slices may be processed as described above instead of the entire data slices. That is, the portions acquired and processed may be of sizes smaller than is necessary to create a complete 2D image. Processing of such smaller portions may be used to determine the scanhead position.

The foregoing operations are discussed in more detail below.

Scanning the Material Volume

The material volume 102 in question is conventionally scanned with any standard ultrasound scanner, using a linear scan for coverage of a comparatively large region, optionally with a tilt of the scanhead 100 to get at hard-to-reach places, e.g., under the rib cage in the case of medical scanning. The image data thereby obtained during the scan may be conventionally collected in any of a variety of forms, i.e. envelope-detected, RF, etc.

Optionally, a rotational scan may be used to image an area under the transducer in the volume of rotation. (The volume immediately adjacent to the transducer's starting position may be included in the rotation.) This provides at least two advantages: First, rotating the scanhead about a central scan-line axis allows repeated views of the same portions of the material volume, which helps correct for any scanhead movement that may occur. Second, when the scanhead is rotated, decorrelation occurs at different rates along the radius out from the axis of rotation (i.e., the radius of the circle of rotation), allowing a more rapid image acquisition. A disadvantage, of course, is that the scan area is only as big as the area scanned by having the axis of rotation at one end of the scanhead.

More than one set of 3D image data may be obtained from different scanning directions. These may be combined by one or more methods discussed below (cross correlation between vertical scan lines and homologous point registration) to position the images with respect to each other. Although orthogonality of the 3D image data is not required, if two sets of 3D image data are orthogonal then each image in one set where the geometry is fixed within the scan plane provides maximal information to aid in positioning the planes in the other data set.

Determining Relative Decorrelation of Specific Portions of the Image

A region of interest is defined in one of the data slices in the series of data slices. A corresponding region of interest is defined on a second slice. The second slice may be immediately adjacent the first slice (e.g., slices 1 and 2) or more widely spaced from the first slice (e.g., slices 1 and 3), depending on the desired sampling rate for the implementation in question.

The amount of correlation between the two corresponding regions of interest is experimentally measured, using conventional techniques, and compared to previously-measured decorrelation for a given transducer. The decorrelation measured may be related to the type of the material 102 as necessary to improve accuracy. The measured decorrelation permits conventional computation of the relative positional difference between the two slices. The same computations are performed for each successive pairs of slices.

Figure 3:
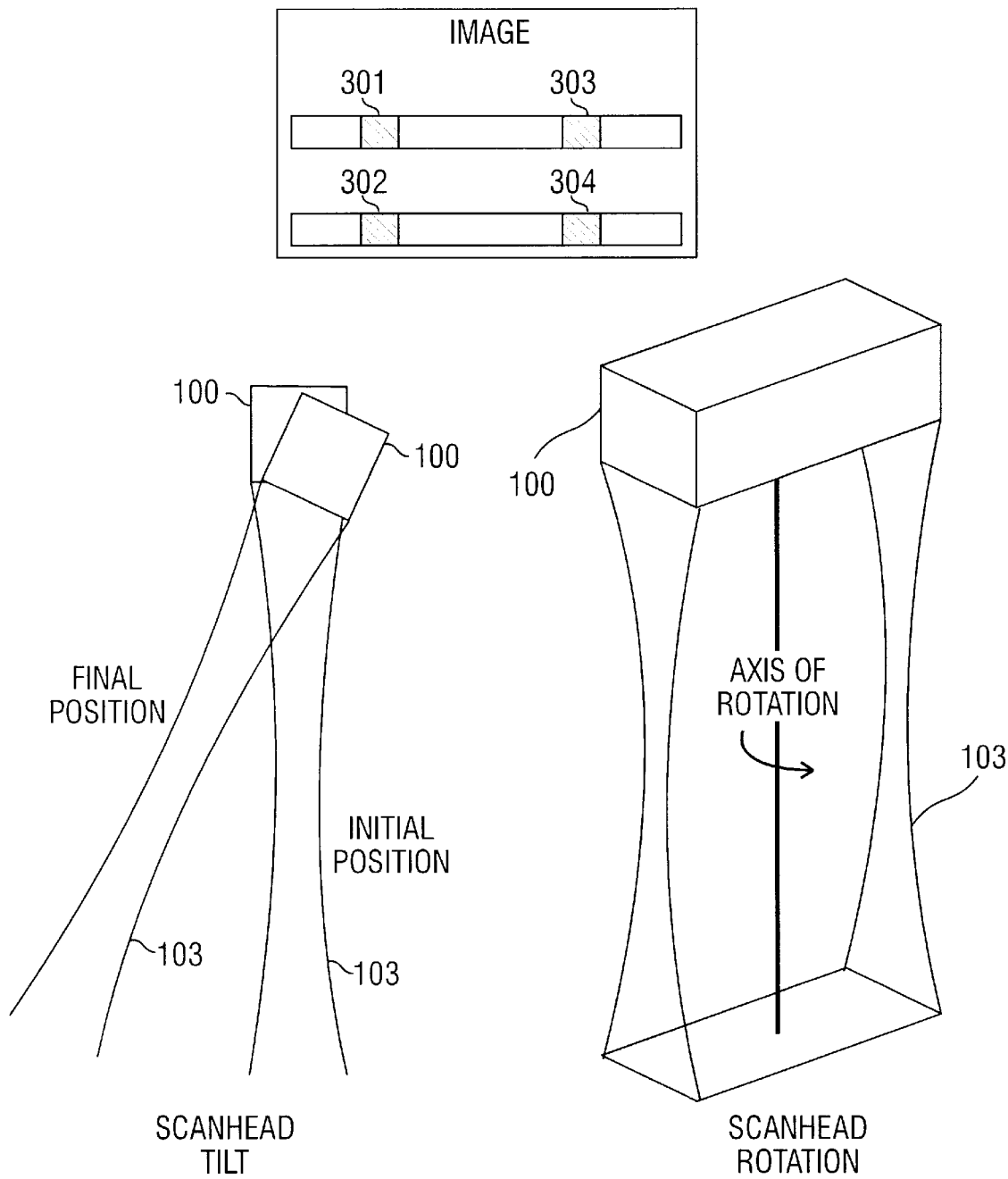
FIG. 3 illustrates a method of monitoring scanhead tilt and rotation.

As shown in FIG. 3, the tilt and rotation of the transducer or scanhead 100 may be monitored by examining the decorrelation rates at various positions of the scanhead within the scan plane. Assume, for example, two specified regions of the material 102 at differing distances from the scanhead 100. If the decorrelation rates differ after appropriate corrections for the beam shape, then it follows that the scanhead 100 is being tilted as shown in FIG. 3. By examining the difference between two regions separated in the lateral direction, rotation of the scanhead may be monitored regardless of where the rotation axis was in the lateral direction. In FIG. 3, the difference in rate between regions 301 and 302 and between 303 and 1 indicates tilting of the scanhead. By examining differences in the lateral direction, i.e. differences between 301 and 303 and between 302 and 304, rotation of the scanhead may be monitored regardless of where the rotation axis was in the lateral direction.

Figure 5:
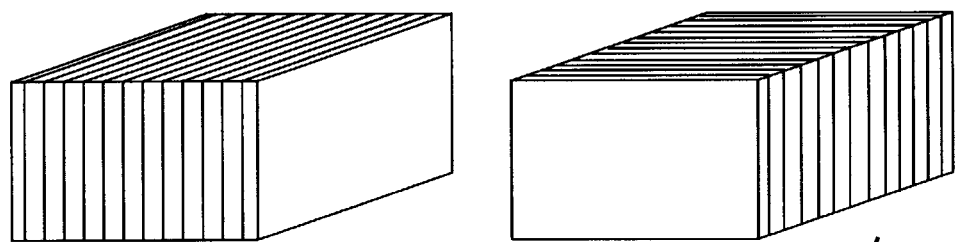
FIG. 5 depicts an approach to slice positioning.
Figure 5:
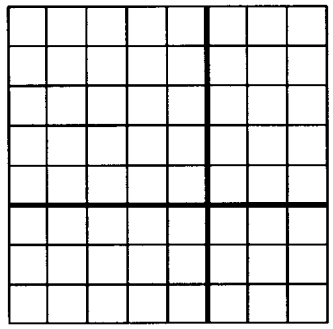
Figure 5:
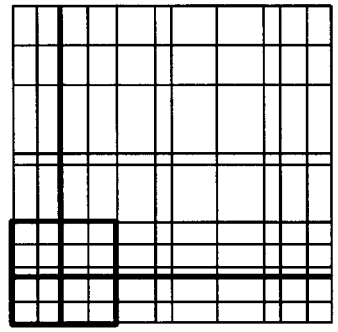

When two data sets from differing look directions are obtained, one method which may be used to position the scan planes in one set is to use the position of the intersection between every pair of scan planes as shown in FIG. 5. This is accomplished by performing a cross correlation between vertical scan lines from each data set (referred to as "A mode correlation). The peak of this correlation defines the intersection of the two planes and any relative vertical movement between the planes. These correlation values are then mapped onto a 2D representation of the area near the intersection. The position of the peak value in this 2D area is the estimated position of the intersection, which defines the position of both planes. The magnitude of this peak relative to the rest of the 2D area can be used as a weighting. Each plane's position will be estimated by using all of its intersections with the orthogonal image. Its final position is determined, then, by the weighted average of these estimates. In this way, a strong feature found on the intersection of two scan planes contributes heavily to the determination of their positions.

Another method which may be applied to any nonparallel image sets taken within the same volume of material is the use of homologous points registration. Points or other structures which can be identified as common to two or more data sets can be used to correctly define the geometric relationship between the image sets. In the case of two orthogonal planes, the process is quite simple. The images are first placed with some arbitrary spacing. As noted in subpart 4.1B above, the geometric relationship within an image (x-z plane of one 3D data set) is known. Therefore if objects identified within an image plane can be similarly identified in the reconstructed x-z plane of the other set then the image plane separation and the vertical position of the image planes can be adjusted to correctly position the plane. The difficulty with the method as described is the need for manual or electronic identification of homologous points.

Once the methods described in subparts 4.1A, B, or C are complete, conventional image-processing techniques are used to position the data slices, utilizing the relative-position information obtained above to correctly position each data slice in a 3D display, which can then be output to a monitor, a hard copy, etc. Optionally, the data slices can be interpolated to produce a 3D image data set with uniform spacing.

Those of ordinary skill having the benefit of this disclosure will appreciate that multiple 3D data sets acquired in this fashion can be conventionally processed to improve the overall image quality of the 2D slices in the 3D sets. Those 2D slices can be redisplayed as two-dimensional images if desired.

On-the-Fly Processing

It is anticipated that in another implementation, by restricting the regions that are measured for motion, it will be possible to minimize the computational time to the point where such monitoring can be performed in real-time. The advantage is that the position information may be computed at a rate faster than the frame rate of the imaging system. Also, it is expected to be possible to set motion criteria which will indicate when the images should be taken to provide an automated way of reducing the number of frames acquired in the 3D data set and fix their spacing to make reconstruction simpler. The processing of RF data for position encoding would then be a separate process which is expected to be more accurate than that possible for the envelope-detected information. In addition, the decorrelation as calculated by these methods may be used to measure the velocity of the scanhead and provide the operator an indication to gauge the rate at which the material should be scanned.

Some Additional Implementations of the Invention

The benefits of eliminating the requirement for encoding of scanhead-position data should not be underestimated. It will be apparent to those of ordinary skill having the benefit of this disclosure that in addition to the elimination of cumbersome manipulation systems and/or position encoding devices, an image-based slice positioning system can provide other motion artifact reduction possibilities and similar capabilities.

For example, it is expected that speckle decorrelation techniques of the kind described above can be used for the correction of respiratory motion when 3D data set is reconstructed. Elevational correction as described above as well as in-plane correction can be used to keep a region of interest stationary in the image.

Figure 4:
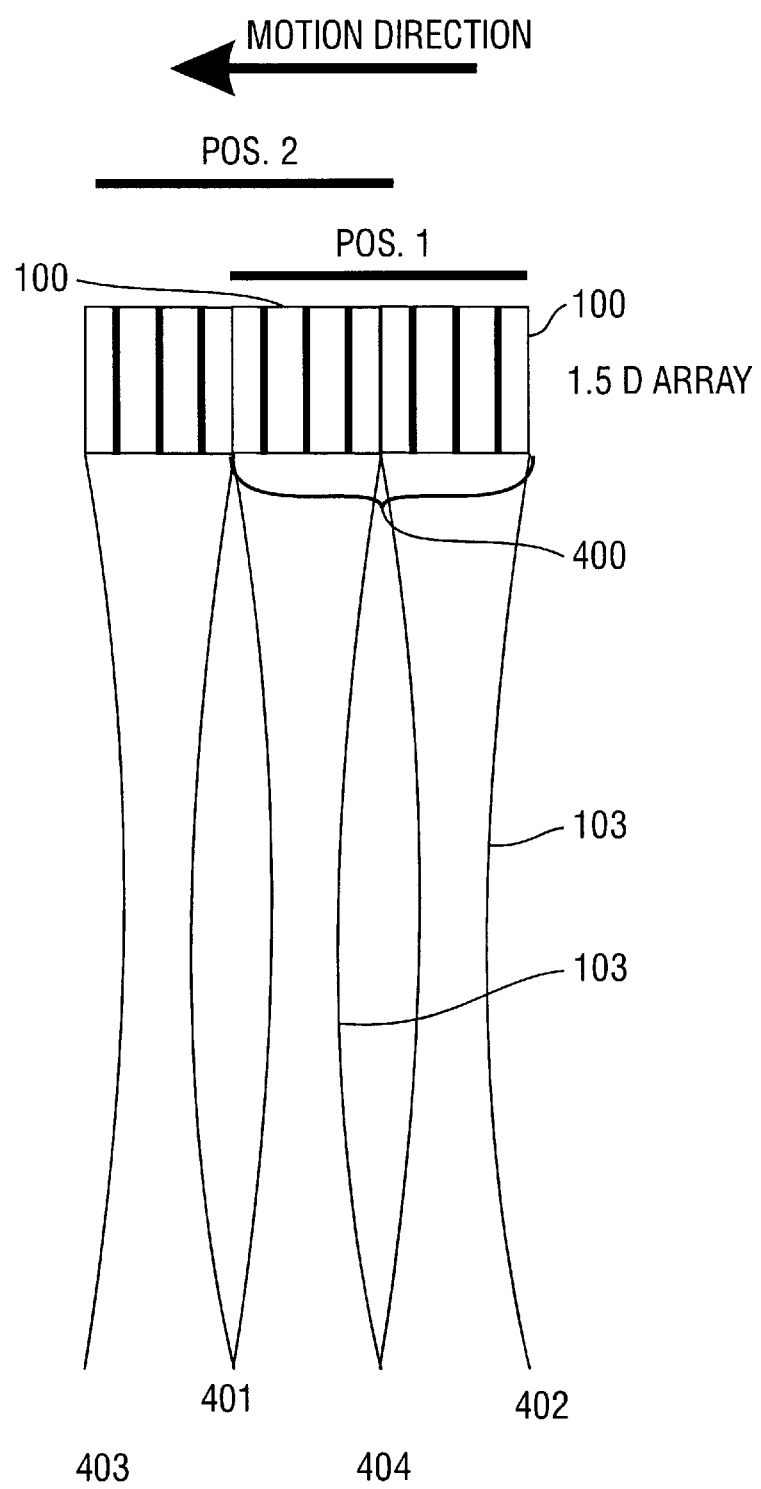
FIG. 4 illustrates an approach to scanhead position tracking.

As another example, it is expected that acquisition of multiple planes, e.g., two, at each location, and correlation of subsequent frames with these can be used to determine when the transducer has moved a fixed distance. This enables not only knowledge of distance traveled but also direction. FIG. 4 depicts how the technique may be applied. At Position 1 two scan planes 103 from a so-called 1.5D scanhead array 400 (which is divided into two linear arrays or potentially used to steer into a second scan plan) are formed at positions 401 and 402. Subsequently the transducer or scanhead moves and as the images are acquired the correlation is calculated. A peak correlation will occur between the previously acquired scan plane 402 and the new plane at position 403 when the scanhead has moved a fixed distance. Note that correlations can be made also for motion in the opposite direction. The placement of planes in the 3D data set could be performed only when the correlation occurred thus placing the planes on a uniform grid space. Or if more planes were needed, the planes which were acquired between correlation points could be spaced uniformly over the distance traveled.

The rate that the speckle pattern is changing can also indicate the presence of phase aberrators in the field of view for the scanhead. By looking at various regions of the image, sudden, inconsistent, regional changes in correlation rates will indicate an aberration of phase. Such mapping could indicate which data to throw out of some images when compounding or reconstructing in 3D or perhaps when and where phase aberration correction would need to be performed in the images.

It is anticipated that the above described techniques can also be used for fine positioning of a scanhead in conjunction with other positioning systems. The latter might be able to monitor the long range motion of the scanhead but lack the fine spatial resolution required for the best 3D reconstructions. Such encoding devices include optical, mechanical, magnetic, electric spark systems, etc. all of which have been used in the past for 3D ultrasound imaging.

It is also anticipated that 2D speckle tracking (Chen, Hein et al. 1991; Chen, Jenkins et al. 1992) can be used to monitor motion in the scan plane between adjacent slices and then measure the decorrelation result. In such an implementation, the 2D speckle tracking identifies the correct vertical and horizontal translation required for placing the adjacent slice with respect to the first. The minimum decorrelation value is determined by comparing selected regions in the two images and the relative positions of the location with minimum decorrelation would indicate the relative vertical and horizontal position of the planes. The minimum decorrelation value which then remained between the slices is the result of the translation in the elevational direction and is expected to be an improved estimate over assuming no vertical or horizontal motion.

Software

FIG. 6 is a block diagram of preliminary software as implemented under the AVS software package of Advanced Visualization Systems of Waltham, Mass. Images are collected from an ultrasound scanner and read into the workstation memory. In this example the data is obtained using a TARGA frame grabber and thus the module TGA Stacker 600 is used. The RGB images are then processed by extract scalar 605 to select one channel and then the 3D data set is sliced using orthogonal slicer 610 and a single 2D plane displayed using image viewer 615 to select regions of interest (ROIs) to be processed for determining the slice separation. The region is selected using crop 620 and redisplayed using another image viewer 625. The pixels contained in the ROI in each image is converted to a 1D vector using ROI to strip 630 and the process repeated using animated integer 635 connected to the orthogonal slicer 610. Each of these strips are then combined in a 2D vector using glue 640. These data are then subsampled using another crop 645 to determine the how many of the image ROIs will be used to compute the position of each image. The controls for determining which images are processed for each slice position calculation are contained in animated integer 650, generate integer 655, and integ_math 660. The cropped output is then analyzed by the correlate module 665 which computes the correlation between successive ROIs, i.e. ROI#1 correlation to ROI#2, ROI#2 to ROI#3, etc. for a one step correlation value. The process is repeated for two, three, etc. step correlations. The correlation curve is then fitted to determine the slice separation for the center two slices in the set used to measure the decorrelation rate. The output of this correlator is displayed by the graph viewer 670 and saved as a file which contains a separation value between each image and the next. This information is then read into fld2rect module 675 and the images from the TGA Stacker 600 are correctly spaced. The correctly positioned images can then be displayed by any desired means such as the ortho 3 slices 680 and geometry viewer 685.

Additional Considerations

In a simple implementation, one can use a sequence of three normally obtained data slices which do not rely on a special transducer construction. In this scenario, the first data slice is obtained and then the second and third as the transducer is translated over the object being imaged. Using the first data slice as a reference, the second data slice will be slightly decorrelated from the first due to transducer motion. If the motion continues in the same direction then the decorrelation that exists between the third data slice acquired and the first will be larger than that between the second and third data slice. If however, the direction changes after data slice 2 is obtained, i.e., the transducer moves back toward the position of data slice 1, then the correlation will be greater between data slices 1 and 3.

The inclusion of specific portions of data slices has significance in at least two ways. First, the selection of data to be used in the positioning of slices can contribute to the success of the positioning. For example, the inclusion of specular reflectors will cause the decorrelation rate to change (slow down) in a manner not related to the transducer motion. Therefore it is helpful to know the characteristics of the material producing the speckle pattern so that the decorrelation of this speckle can be used to determine the position of slices. Second, conventional criteria can be used to produce images of specific tissue types and characteristics or in the compounding of multiple sets of data slices to produce improved images as in the case of speckle reduction or imaging of connective tissue (specular reflectors).

We claim:

1. A methods executed by a machine, of displaying a 3D image of a human tissue volume, said method comprising:
   (a) receiving a plurality of data sets, referred to as data slices, each said data slice representing a respective 2D slice of said tissue volume, said plurality of data slices having been generated by ultrasound scanning of said tissue volume;
   (b) defining (1) one or more regions within one of said data slices, referred to as regions 1a, 1b, and so on, within data slice 1, and (2) one or more regions within another of said data slices, referred to as regions 2a, 2b, and so on, within data slice 2;
   (c) performing a process of speckle decorrelation measurement to determine respective amounts of correlation between regions 1a and 2a, regions 1b and 2b, and so on;
   (d) utilizing said respective amounts of correlation to compute a relative positional difference vector representative of a relative positional difference between data slice 1 and data slice 2;
   (e) storing in a memory device (1) a representation of at least a portion of said data slice 1, (2) a representation of at least a portion of said data slice 2, and (3) said relative positional difference vector;
   (f) computing, from said relative positional difference vector, a relative position of each of said data slice 1 and said data slice 2 within a 3D image of the material; and
   (g) displaying said 3D image on a visual display.

2. A method, executed by a machine, of creating a memory containing a data structure encoding a series of two-dimensional representations of a material, said method comprising:
   (a) receiving a plurality of data sets, referred to as data slices, each said data slice representing a respective slice of said material;
   (b) defining (1) one or more regions within one of said data slices, referred to as one or more regions within data slice 1, and (2) one or more regions within another of said data slices, referred to as one or more regions within data slice 2;
   (c) measuring respective amounts of correlation between said one or more regions within data slice 1 and said one or more regions within data slice 2;
   (d) utilizing said respective amounts of correlation to compute a relative positional difference vector representative of a relative positional difference between data slice 1 and data slice 2; and
   (e) writing to said memory (1) a representation of at least a portion of said data slice 1, (2) a representation of at least a portion of said data slice 2, and (3) said relative positional difference vector.

3. The method of claim 2, wherein at least some of said data slices are smaller in size than required to specify a two-dimensional image.

4. The method of claim 2, wherein said data slices are received from a scanhead having a position relative to the material, and further comprising determining said position by performing a computation utilizing respective portions of at least two of said data slices.

5. The method of claim 2, wherein said data slices are received from a scanhead that is being moved relative to the material at a rate referred to as a scanning rate, and further comprising determining, from respective portions of at least two of said data slices, one or more of (i) a total number of data slices to be acquired, and (ii) a desired scanning rate.

6. The method of claim 2, wherein:
   (1) at least some of said plurality of data slices are generated by scanning at least a portion of said material with a beam of coherent energy; and
   (2) said material comprises a plurality of energy scatterers.

7. The method of claim 6, wherein said energy scatterers reflect coherent energy in a speckled pattern.

8. The method of claim 2, further comprising:
   (1) computing, from said relative positional difference vector, a relative position of each of said data slice 1 and said data slice 2 within a 3D image of the material; and
   (2) displaying said 3D image on a visual display.

9. The method of claim 2, wherein said measurement of respective amounts of correlation is performed by a process of speckle decorrelation measurement.

10. The method of claim 2, wherein said 2D data slices are generated by an ultrasound scan of said material.

11. The method of claim 2, wherein said material is a tissue volume.

12. The method of claim 2, wherein
   (1) said measurement of an amount of correlation between a first one of said one or more regions in data slice 1 and a region in data slice 2 is performed by (i) locating one of said one or more regions in data slice 2 that has a minimum decorrelation value, referred to as a minimum-decorrelation region, and (ii) determining two orthogonal in-plane components of a vector between said minimum-decorrelation region and said first one of said regions in data slice 1; and
   (2) said utilization of said amount of correlation is performed by utilizing, as said measurement of said amount of correlation, an out-of-plane component of said vector that is orthogonal to said in-plane components.

13. A method, executed by a machine, of displaying a 3D image of a human tissue volume, said method comprising:
   (a) receiving a plurality of data sets, referred to as data slices, each said data slice representing a respective 2D slice of said tissue volume;
   (b) defining (1) one or more regions within one of said data slices, referred to as one or more regions within data slice 1, and (2) one or more regions within another of said data slices, referred to as one or more regions within data slice 2;
   (c) performing a process of speckle decorrelation measurement to determine respective amounts of correlation between said one or more regions in data slice 1 and said one or more regions in data slice 2;
   (d) utilizing said respective amounts of correlation to compute a relative positional difference vector representative of a relative positional difference between data slice 1 and data slice 2.

14. A program storage device having encoded instructions for performing the method of any of claims 1 through 13.

15. A machine containing a memory having a data structure created by the method of any of claims 2 through 12.

16. A method in accordance with claim 2, wherein said data slices are obtained using an imaging transducer.

17. A method in accordance with claim 16, further comprising:
   determining that motion of said transducer has changed by detecting an increase in the correlation of at least one data slice relative to at least one other previously obtained data slice.

18. A method in accordance with claim 2, wherein said step of computing said relative positional difference vector comprises image processing to find regions of coherent speckle.

19. A method in accordance with claim 2, wherein said step of computing said relative positional difference vector comprises image processing to extract data which do not represent coherent speckle.

20. A method in accordance with claim 2, wherein said step of computing said relative positional difference vector comprises image processing to extract data which do not decorrelate rapidly.

21. A method in accordance with claim 2, wherein said step of computing said relative positional difference vector using characteristics of data in a data slice to predict the behavior in an out-of-plane direction to include data in the positioning of slices.

22. A method in accordance with claim 2, wherein said step of computing said relative positional difference vector comprises using characteristics of data in a data slice to predict the behavior in an out-of-plane direction to exclude data in the positioning of slices.

23. A method of generating image views of imaged material, which views reveal specific characteristics of said material, comprising:
   (a) receiving a plurality of data sets, referred to as data slices, each data slice representing a respective 2-D image of said material;
   (b) image processing said data slices to identify regions of coherent speckle therein;
   (c) generating said image views using slices having regions of coherent speckle therein.

24. A method of generating image views of imaged material, which views reveal specific characteristics of said material, comprising:
   (a) receiving a plurality of data sets, referred to as data slices, each data slice representing a respective 2-D image of said material;
   (b) image processing said data slices to extract data which do not represent coherent speckle;
   (c) generating said image views using said processed data slices.

25. A method of generating image views of imaged material, which views reveal specific characteristics of said material, comprising:
   (a) receiving a plurality of data sets, referred to as data slices, each data slice representing a respective 2-D image of said material;
   (b) image processing said data slices to assess decorrelation rates in 3-D;

(c) selecting data slices for said image views based on said assessed decorrelation rates.

26. A method in accordance with claim 24, wherein said step (b) of image processing to extract data which do not represent coherent speckle comprises detecting and subtracting data corresponding to reverberations.

27. A method in accordance with claim 25, wherein said step (c) of selecting data slices based on assessed decorrelation rates comprises assessing decorrelation rates in adjacent slices to identify sets of slices in which decorrelation rate corresponds to artifacts of multiple scattering, refraction, diffraction, or shadowing.

28. A method in accordance with claim 25, wherein said step (c) of selecting data slices based on assessed decorrelation rates comprises assessing decorrelation rates in adjacent slices to identify regions of adjacent slices decelerating more rapidly than remaining regions in said adjacent slices.

29. A method as in any of claims 26, 27, or 28, further comprising the step (d) of generating image views using data slices and portions of data slices which are relatively free from artifacts.

30. A method as in any of claims 26, 27, or 28, further comprising the step (d) of generating image views using data slices which reveal desired characteristics of said imaged material.

31. A method in accordance with claim 2, wherein said plurality of data sets include data slices from at least two different look directions.

32. A method in accordance with claim 31, wherein all but one of said plurality of data sets can include only one data slice.

33. A method in accordance with claim 32, further comprising the step (f) of spatially aligning said plurality of data sets.

34. A method in accordance with claim 33, further comprising the step (g) of refining said relative positional difference vectors between adjacent slices.

35. A method in accordance with claim 34, wherein said step (f) of spatial alignment further comprises the steps of:

(h) of cross-correlating comparisons of vertical lines between two data sets to locate a most likely intersection point of two data slices from said two data sets; and (i) utilizing said intersection point to position said data sets.

* * * * *

UNITED STATES PATENT AND TRADEMARK OFFICE
CERTIFICATE OF CORRECTION

PATENT NO. : 6,059,727
DATED : May 9, 2000
INVENTOR(S) : Fowlkes et al.

It is certified that error appears in the above-identified patent and that said Letters Patent is hereby corrected as shown below:

Column 8, claim 1,
Line 16, please delete "A methods" and insert --A method-- therefor.

Signed and Sealed this

Fourth Day of December, 2001

Attest:

*Attesting Officer*

NICHOLAS P. GODICI
*Acting Director of the United States Patent and Trademark Office*